United States Patent
Buchlovic et al.

(10) Patent No.: US 10,919,988 B2
(45) Date of Patent: Feb. 16, 2021

(54) PROCESS FOR MAKING SUGAMMADEX

(71) Applicant: Synthon B.V., Nijmegen (NL)

(72) Inventors: Marian Buchlovic, Blansko (CZ); Lenka Cernova, Blansko (CZ)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 16/624,708

(22) PCT Filed: Jun. 29, 2018

(86) PCT No.: PCT/EP2018/067707
§ 371 (c)(1),
(2) Date: Dec. 19, 2019

(87) PCT Pub. No.: WO2019/002610
PCT Pub. Date: Jan. 3, 2019

(65) Prior Publication Data
US 2020/0216575 A1    Jul. 9, 2020

(30) Foreign Application Priority Data
Jun. 30, 2017  (EP) .................................... 17179134

(51) Int. Cl.
*C08B 37/16* (2006.01)
*C08B 37/00* (2006.01)
(52) U.S. Cl.
CPC ...... *C08B 37/0012* (2013.01); *C08B 37/0003* (2013.01)
(58) Field of Classification Search
None
See application file for complete search history.

(56) References Cited
U.S. PATENT DOCUMENTS

2019/0185589 A1    6/2019  Overeem

FOREIGN PATENT DOCUMENTS

| WO | WO/0140316 A1 | 6/2001 |
| WO | WO2012/025937 A1 | 3/2012 |
| WO | WO2014/125501 A1 | 8/2014 |
| WO | WO2016/194001 A1 | 12/2016 |
| WO | WO2017/144734 A2 | 8/2017 |

OTHER PUBLICATIONS

Chmurski et al., "An Improved Synthesis of 6-Deoxyhalo Cyclodextrins via Halomethylenemorpholinium Halides Vilsmeier-Haack Type Reagents," Tetrahedron Letters, Elsevier, Amste.

*Primary Examiner* — Layla D Berry
(74) *Attorney, Agent, or Firm* — Buscher Patent PLLC

(57) ABSTRACT

The invention deals with a novel process for making intermediates of the pharmaceutically useful product Sugammadex of formula (1).

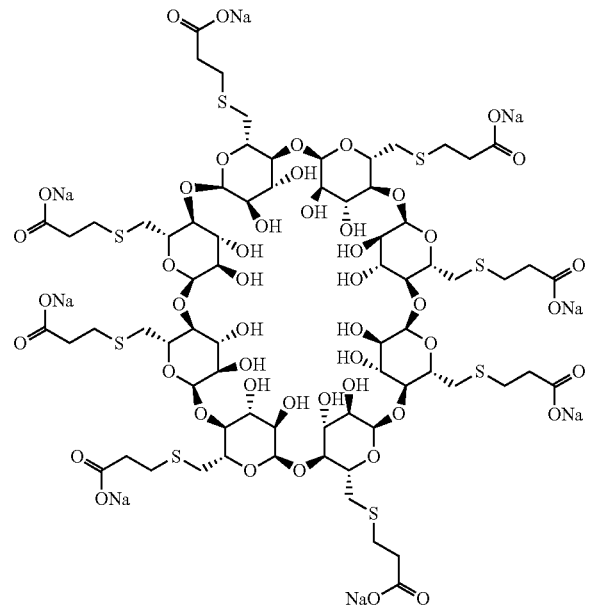

15 Claims, No Drawings

PROCESS FOR MAKING SUGAMMADEX

The invention relates to a novel process for making the pharmaceutical product Sugammadex.

OVERVIEW OF THE PRIOR ART

Sugammadex, i.e. 5-Cyclooctakis-(1→4)-[6-S-(2-carboxyethyl)-6-thio-alfa-D-glucopyranosyl] of formula (1),

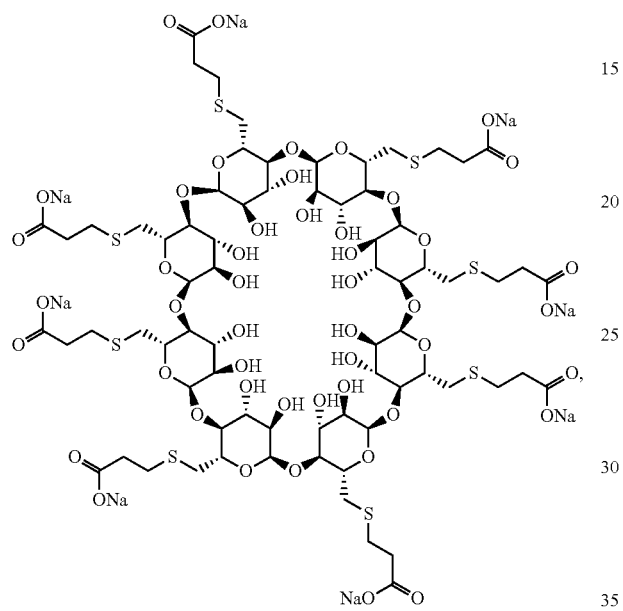

(1)

is a modified γ-cyclodextrin.

Sugammadex is the first selective relaxant binding agent for reversal of neuromuscular blockade by the agent rocuronium or vecuronium in general anesthesia. It was approved in 2008 by EMEA. It is marketed in the form of a sterile solution for intravenous injection under the brand name Bridion®. Sugammadex was first disclosed in WO20001040316.

WO20001040316 discloses a process for making Sugammadex as depicted below:

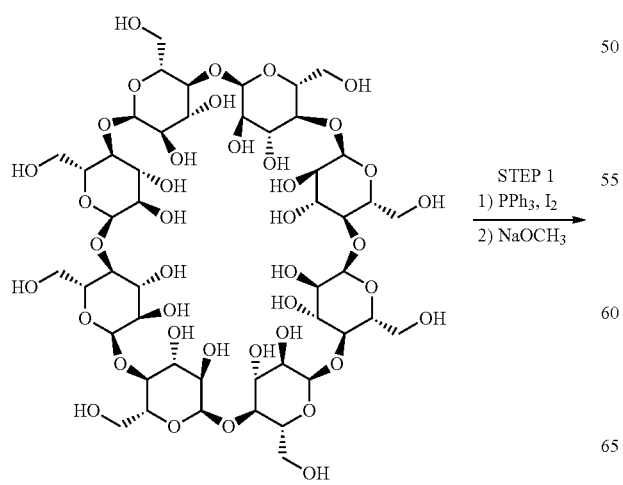

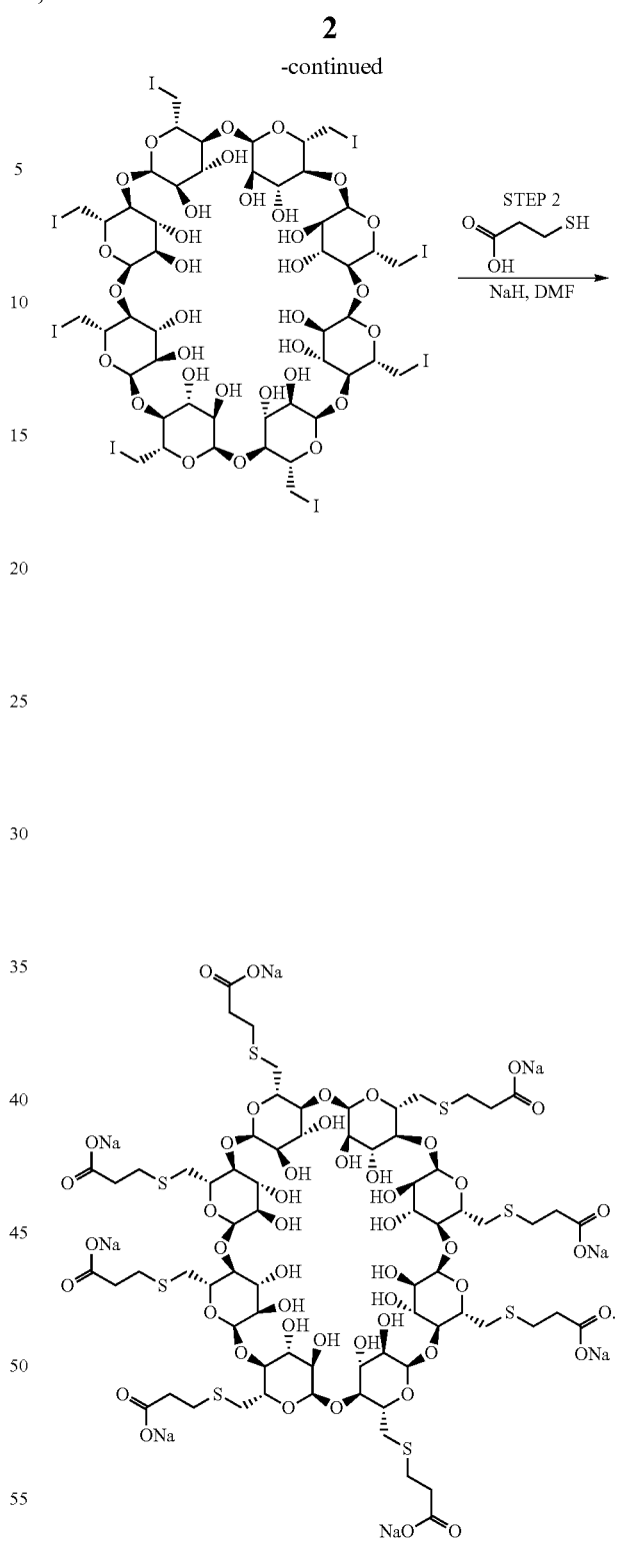

The first step involves the in situ preparation of a Vilsmeier-Haack reagent by the reaction of dimethylformamide (DMF), triphenylphosphine ($PPh_3$) and iodine to form an activated γ-cyclodextrin. Triphenylphosphine oxide is formed as a by-product of the first step. The removal of this by-product from the reaction mixture is very difficult. This by-product will react in the second step to form the impurity of formula (2), (2)

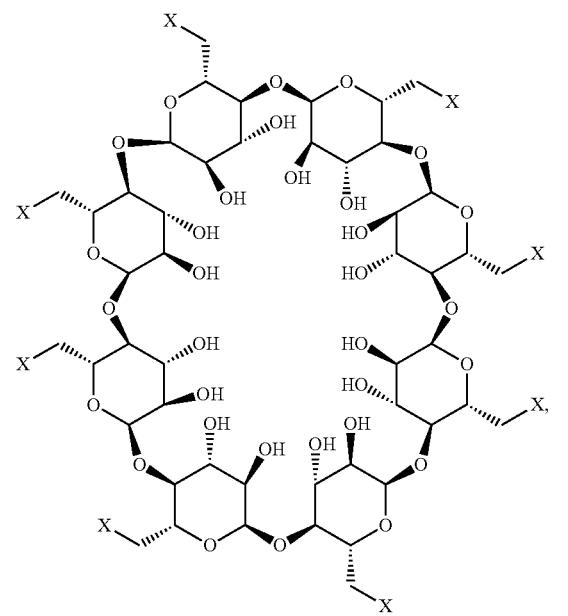

(3)

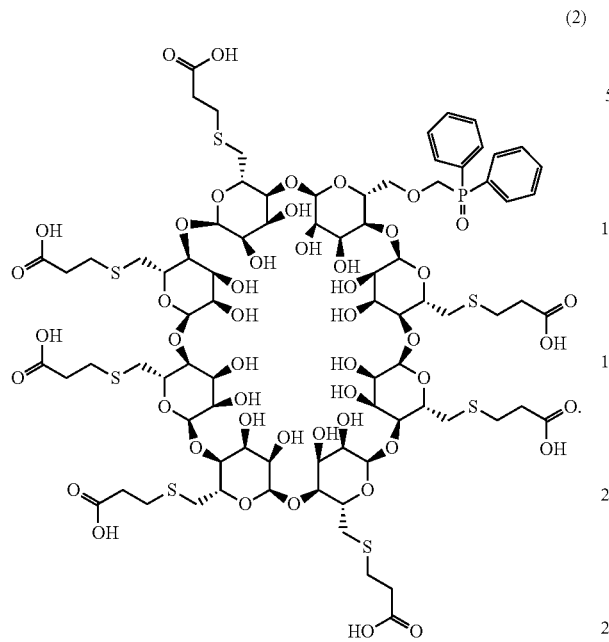

The second step involves the reaction of the functionalized γ-cyclodextrin with 3-mercaptopropionic acid in presence of NaH and DMF to give Sugammadex. The yield of the reaction is low (43%).

WO2012025937 describes the first step of the synthesis using different reagents than WO20001040316. According to the applicant the use of $PX_5$ or $PX_3$, where X is F, Cl, Br, I instead of $PPh_3/I_2$ results in better yield and purity of the product of step 1. The use of $PX_5$ and $PX_3$ is not desirable because of their toxicity; furthermore these compounds are corrosive and produce fumes, making its handling on large scale more difficult.

WO2014125501 discloses preparation of Sugammadex involving reaction of γ-cyclodextrin with phosphorus halide and subsequent reaction of the product with an alkali metal alkoxides. These alkoxides are flammable and therefore difficult to handle during production.

WO2016194001 discloses preparation a process comprising reaction of γ-cyclodextrin with oxalyl halide and subsequent transformation of the reaction product to Sugammadex. Oxalyl halide is a toxic liquid liberating a toxic, corrosive gas upon contact with water.

Therefore, there exists a need for an improved and efficient process for the preparation of Sugamadex.

BRIEF DESCRIPTION OF THE PRESENT INVENTION

The subject of the present invention is a novel process for preparation of Sugamadex comprising:
a. Mixing of γ-cyclodextrin with $CX_4$, in the presence of triphenylphosphine and N-methyl-2-pyrrolidone;
b. Treating the reaction product with a base to provide corresponding 6-per-deoxy-6-per-halo-γ-cyclodextrin compound of formula (3), wherein X is Cl or Br or I;
c. Reacting compound of formula (3) with 3-mercaptopropionic acid in the presence of a sodium base to provide Sugammadex of formula (1), (1)

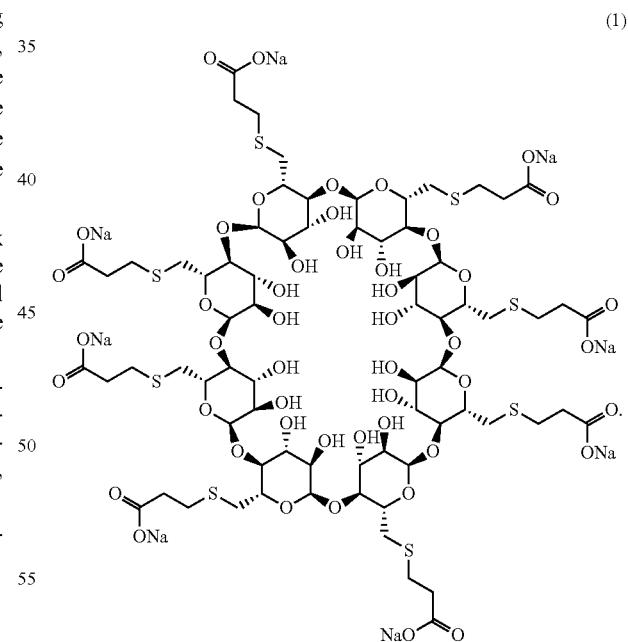

DETAILED DESCRIPTION OF THE PRESENT INVENTION

The invention provides a process for preparation of Sugammadex comprising:
a. Mixing of γ-cyclodextrin with $CX_4$, in the presence of triphenylphosphine and N-methyl-2-pyrrolidone;

b. Treating the reaction product with a base to provide corresponding 6-per-deoxy-6-per-halo-γ-cyclodextrin compound of formula (3),

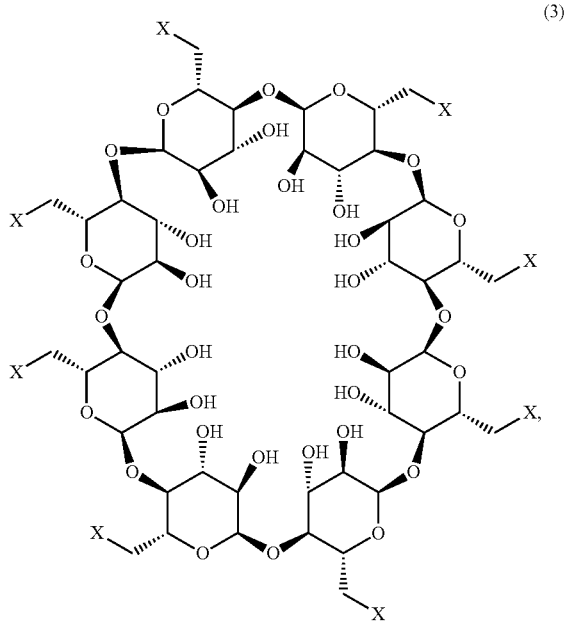

(3)

wherein X is Cl or Br or I c. Reacting compound of formula (3) with 3-mercaptopropionic acid in the presence of a sodium base to provide Sugammadex of formula (1),

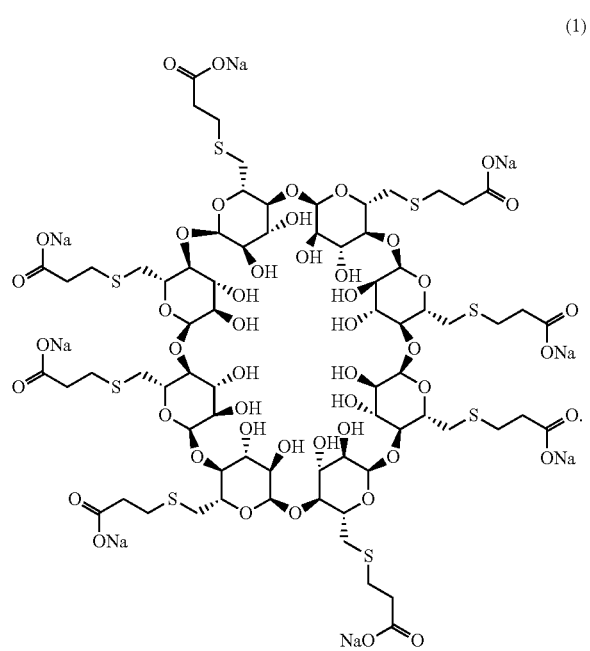

(1)

The starting material of step a. is γ-cyclodextrin. This cyclodextrin is commercially available.

In the step a. γ-cyclodextrin is mixed with triphenylphosphine and N-methyl-2-pyrrolidone to form a mixture. $CX_4$, wherein X is Br or Cl or I, preferably Br, is added to the mixture. The molar ratio can be between γ-cyclodextrin and $CX_4$ is between 1:8 and 1:20, preferably the molar ratio is between 1:10 and 1:15, more preferably the molar ratio is between 1:10 and 1:12. Optionally an organic solvent might be used. As an organic solvent dichloromethane or methyl-tert-butyl ether or toluene or acetonitrile or THF can be used. Preferably dichloromethane might be used. $CX_4$ is preferably added slowly, i.e. within 10, 20, 30, 40, 50 or 60 minutes preferably at a temperature below 30° C. The mixture is then heated at a temperature between 30° C. and 60° C., preferably between 45 to 55° C., most preferably at 50° C. and stirred at this temperature for 1 to 5 hours, preferably for 2 hours.

We have surprisingly found that the presence of N-methyl-2-pyrrolidone is crucial for the reaction to be completed. When no N-methyl-2-pyrrolidone is present, the reaction mixture after reaction between γ-cyclodextrin and the halogenating reagent $CX_4$, where X is Br or Cl or I, preferably Br, contains less than 55% (HPLC IN) of the compound of formula (3) depending on reaction conditions. In the presence of N-methyl-2-pyrrolidone the mixture after reaction between γ-cyclodextrin and the halogenating reagent contains more than 95% of the compound of formula (3).

The use of $CX_4$, wherein X is Br or Cl or I, also reduces the amount of corrosive halogen acid (HX) that is a byproduct in the prior art processes.

Advantageously, $CBr_4$ and $CI_4$ are solid crystalline compounds that are easy to handle.

The process of the invention also reduces the amount of triphenylphosphine used in the reaction and thereby also reduces the amount of triphenylphosphine oxide which is formed as a by-product. The removal of this by-product from the reaction mixture is very difficult since it reacts with γ-cyclodextrin to form an impurity that is difficult to purify from the final product.

The preferred molar ratio of γ-cyclodextrin to triphenylphosphine ranges from 1:10 to 1:20, preferably it is 1:15. The concentration of γ-cyclodextrin in N-methyl-2-pyrrolidone ranges from 0.1 to 1 g/ml, preferably the concentration of γ-cyclodextrin in N-methyl-2-pyrrolidone is 0.4 g/ml. The reaction progress can be monitored by any suitable analytical method, known by the skilled person.

After the reaction is completed the mixture is cooled at a temperature between −10° C. and 20° C., preferably between 0 and 5° C. To the mixture a base is added (reaction step b.) while the temperature of the mixture is maintained below 20° C. The molar ratio between the γ-cyclodextrin and the base is between 1:12 and 1:50, preferably it is between 1:15 and 1:25, more preferably between 1:16 and 1:18.

As a base, organic bases such as amines, for example methylamine, triethylamine, diethylamine or inorganic bases such as water solution of ammonia (ammonium hydroxide), sodium hydroxide, potassium hydroxide, sodium carbonate, potassium carbonate, sodium hydrogencarbonate, potassium hydrogencarbonate might be used. Preferably 20-30% water solution of ammonia is used. Comparing to other bases known from the prior art, the water solution of ammonia results in a reaction comprising less by-products compared to stronger bases. In addition, the reaction by-products are soluble in water and can be easily removed from the reaction mixture.

An alcohol, such as methanol, ethanol, propanol, isopropanol, butanol preferably methanol, is added to the reaction mixture, at a temperature between 20° C.-40° C., preferably between 20-25° C. To the resulting mixture water is added. The mixture is cooled at −10-10° C., preferably at 0-5° C. and stirred for 10-60 minutes to precipitate the solid product.

The compound of formula (3) subsequently reacts in step c. with 3-mercaptopropionic acid in the presence of a sodium base to provide Sugammadex of formula (1) by a process known from the prior art.

The molar ratio of 3-mercaptopropionic acid and compound of formula (3) can be between 8:1-25:1, preferably it is between 15:1 and 22:1, more preferably it is between 16:1 and 19:1. As a sodium base NaOH or NaH or Na alkoxides or other sodium bases known from prior art can be used. Preferably water solution of NaOH is used, more preferably 3-7 Molar solution is used. The molar ratio between the base and compound of formula (3) can be between 16:1 and 40:1, preferably between 25:1 and 37:1, more preferably between 30:1 and 35:1. The reaction step c. can run in an organic solvent for example in N-methyl-2-pyrrolidone or dimethylacetamide or dimethylformamide or dimethylsulfoxide. The organic solvent can be optionally used in a mixture with water. The presence of water further improves yields of the reaction and purity of the product. The ratio between water and the organic solvent can be between 1:0.8 and 1:3 (vol:vol), preferably it is 1:1.1. The reaction mixture can be optionally heated at a temperature between 40° C. and the reflux temperature of the solvent. In case the organic solvent is used in combination with water, water can be added to the reaction mixture before or after heating of the mixture, preferably it is added after heating the mixture. The mixture is stirred at the temperature between 40° C. and the reflux temperature of the solvent for 1 to 10 hours, preferably for 2 to 5 hours. After the reaction is completed a water miscible organic solvent, for example DMSO or alcohols, such as methanol or ethanol or isopropanol, is added. The ratio between the organic solvent used in step c. and the water miscible organic solvent added after the reaction is completed can be between 2:0.7 and 2:1.5 (vol:vol), preferably it is 2:1.

The mixture is cooled to a temperature between −10° C. and 25° C., preferably between 0 and 5° C., the mixture is stirred at this temperature for 10 to 60 minutes, preferably for 20 to 35 minutes to precipitate Sugammadex from the mixture. The precipitated solid might be separated by a suitable process known by the skill person, for example filtration or centrifugation.

The compound of formula (3) prepared by the process of the presented invention might be purified by using a process comprising the steps of:
1. Suspending the compound of formula (3) in an alcohol, wherein the alcohol comprises between 3 and 30% (vol/vol) of water;
2. Heating the mixture;
3. Isolating the compound of formula (3).

The alcohol used in step I. is preferably methanol, ethanol, propanol, isopropanol most preferably it is methanol or ethanol. The alcohol comprises between 3 and 30% (vol/vol) of water, preferably it comprises between 4 and 7%, most preferably 5% (vol/vol) of water.

The concentration of compound of formula (3) in an alcohol might range from 0.08 to 0.8 g/ml, preferably ranges from 0.1 to 0.5 g/ml, most preferably it is 0.2 g/ml.

The mixture obtained from step I. is heated in step II. at a temperature between 45° C. and the reflux temperature of the solvent, preferably between 50 and 60° C. for 10 to 60 minutes, preferably for 20 to 40 minutes. The isolating step III. comprises cooling of the mixture to a temperature between −10 and 10° C., preferably between 0 and 5° C. and stirred at this temperature for 10 to 60 minutes, preferably for 30 minutes. The precipitated solid might be separated by a suitable process known by the skill person, for example filtration or centrifugation.

Using the process of the present invention the amount of triphenyl phosphine oxide in obtained compound of formula (3) is decreased comparing to processes described in the prior art.

The following examples are intended to illustrate the scope of the present invention but not to limit it thereto.

EXAMPLES

Example 1: Preparation of Compound of Formula (3)

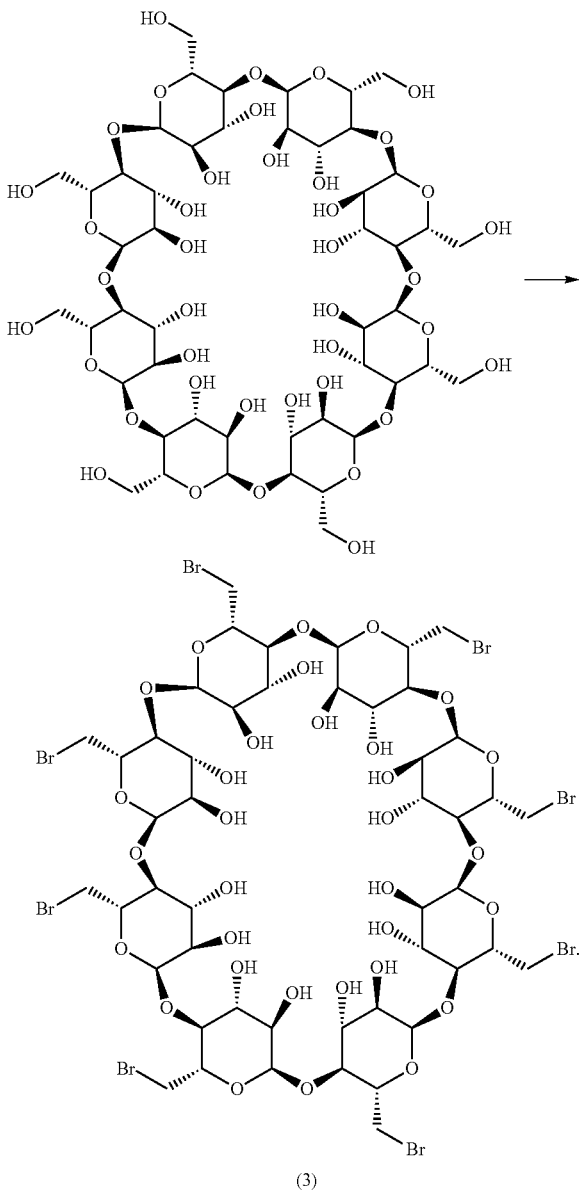

(3)

1000 ml of N-Methyl-2-pyrrolidinone was mixed with 200 g of γ-Cyclodextrin. The mixture was cooled to 0-5° C. 607 g of Triphenylphosphine was added in one portion. The mixture was stirred at temp 0-5° C. for 10 min.

To the mixture, solution of 562 g of tetrabromomethane in 240 ml of dichloromethane was slowly added. The rate of the addition was controlled to keep the reaction temperature below 30° C. The mixture was then heated at 50° C. for 2 hours. After the reaction completion, the mixture was cooled to 0-5° C. and then 400 ml of 25% (vol/vol) aqueous ammonia was slowly added. The rate of the addition was controlled to keep the reaction temperature below 20° C. 800 ml of MeOH was added, followed by slow addition of 500 ml of water. The mixture was stirred for 10 min. at 20-30° C. and then cooled to 0-5° C., stirred for 30 min. and filtered. The filtration cake was washed with 3×500 ml of cold MeOH (3×500 mL). Compound of formula (3) was prepared in overall yield 84% and purity 99.5% (HPLC IN). The content of triphenylphosphine oxide impurity was 7% (wt/wt, based on compound (3)).

Example 2: Preparation of Compound of Formula (3)

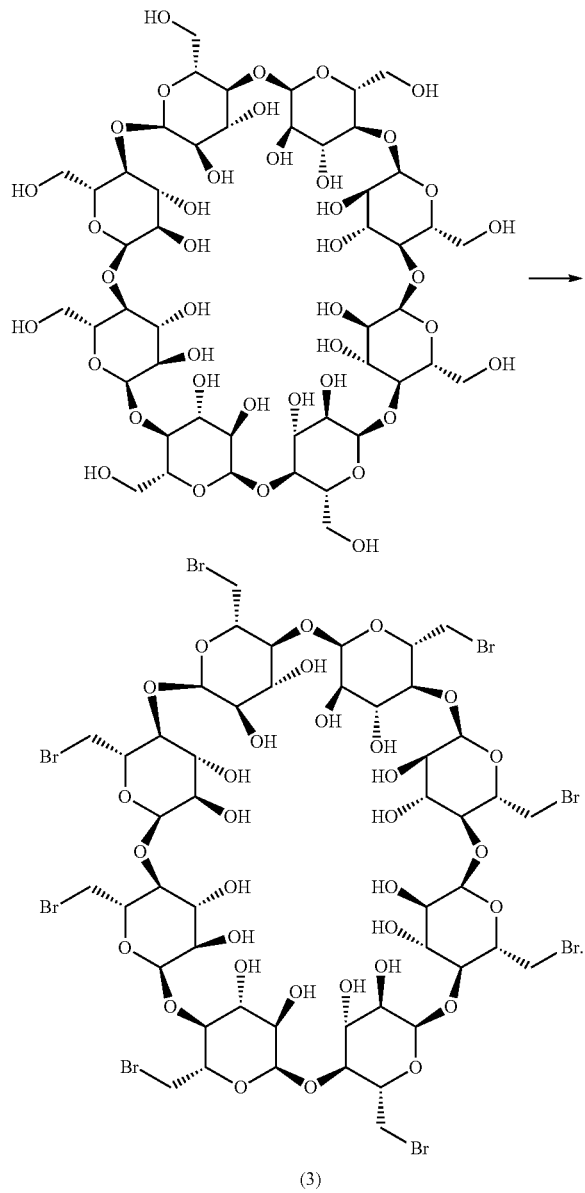

(3)

1000 ml of N-Methyl-2-pyrrolidinone was mixed with 200 g of γ-Cyclodextrin. The mixture was cooled to 12-17° C. 607 g of Triphenylphosphine was added in one portion.

To the mixture, solution of 562 g of tetrabromomethane in 240 ml of methyl-tert-butyl ether (MTBE) was slowly added. The rate of the addition was controlled to keep the reaction temperature below 30° C. The mixture was then heated at 50° C. for 2 hours. After the reaction completion, the mixture was cooled to 0-5° C. and then 400 ml of 25% (vol/vol) aqueous ammonia was slowly added. The rate of the addition was controlled to keep the reaction temperature below 20° C. 1000 ml of MeOH was added, followed by slow addition of 600 ml of water. The mixture was stirred for 10 min. at 20-30° C. and then cooled to 0-5° C., stirred for 30 min and filtered. The filtration cake was washed with 3×500 ml of cold MeOH (3×500 mL). Compound of formula (3) was prepared in overall yield 84% and purity 99.5% (HPLC IN). The content of triphenylphosphine oxide impurity was 7% (wt/wt, based on compound (3)).

Example 3: Preparation of Compound of Formula (3)

0.477 g of triphenylphosphine, 0.575 g of tetrabromomethane and of 0.1 g of γ-Cyclodextrin were mixed with 2 ml of a solvent specified in Table 1. For entries 1 to 3 no N-methyl-2-pyrrolidone was added, entry 4 was done in a presence of 0.5 ml of N-methyl-2-pyrrolidone (NMP). The mixture was stirred at room temperature for 60 minutes then heated for 3 hours at 50° C. The samples of reaction mixtures were sampled into a mixture of DMF, methanol and aqueous solution of ammonia and analyzed by HPLC, reaction conversion is summarized in Table 1.

TABLE 1

| Entry | Solvents | Reaction conversion |
| --- | --- | --- |
| 1 | Pyridine | 53% |
| 2 | DMF | 42% |
| 3 | DMF/Pyridine | 19% |
| 4 | Dichloromethane | >99% |

Example 4: Purification of Compound of Formula (3)

26.84 g of per-bromo-γ-cyclodextrin prepared according to example 1 with content of triphenylphosphine oxide 7% (wt/wt on compound of formula (3)) was suspended in 140 ml of MeOH comprising 5% of water. The mixture was heated at 60° C. for 30 min., then cooled to 0-5° C., stirred for 30 minutes and filtered. The filtration cake was washed with MeOH The product was dried at room temperature to give 24.19 g of compound of formula (3). The content of tri-phenylphosphine oxide in the isolated product was 0.13% (wt/wt on compound of formula (3)).

Example 5: Preparation of Sugammadex 5 g of compound of formula (3) prepared according to example 1 was suspended in 40 ml of DMSO and stirred at 25° C. until full dissolution. 16 ml of 5M aqueous NaOH solution was cooled in ice-water bath. To this NaOH water solution 3.63 ml of 3-mercaptopropanoic acid was added drop-wise during 10 minutes. Temperature of the reaction mixture was kept below 10° C. The mixture was heated to 40° C., followed by addition of compound (3) solution in DMSO. The mixture was heated at 45-50° C. for 3 hours. To the mixture 28 ml of water was slowly added followed by 10 ml of DMSO. The mixture the mixture was cooled to 0-5° C., stirred for 30 min. and filtered. The filtration cake was washed with cold acetone and the product was dried at room temperature to provide Sugammadex in almost 100% yield.

Example 6: Preparation of Sugammadex 1 g of compound of formula (3) prepared according to example 1 was suspended in 8 ml of dimethylsulfoxide and stirred at 25° C. until full dissolution. 3.22 ml of 5M Sodium hydroxide solution in water was cooled in ice-water bath. To this NaOH water solution, 0.73 ml of 3-mercaptopropanoic acid was added dropwise during 10 minutes. Temperature of the reaction mixture was kept below 10° C. Compound (3) solution in dimethylsulfoxide was added and temperature of the reaction mixture was kept below 20° C. The mixture was then heated to 45-50° C. As soon as the temperature of the mixture was reached, 6 ml of water was added and the reaction mixture was stirred for 3 hours at 45-50° C. To the mixture, 4 ml of dimethylsulfoxide were added. The mixture was cooled to 0-5° C., stirred for 30 min. and filtered. The filtration cake was washed with cold acetone and the product was dried at room temperature to provide Sugammadex in almost 100% yield.

Example 7: Preparation of Sugammadex 1 g of compound of formula (3) prepared according to example 1 was suspended in 8 ml of N-methyl-2-pyrrolidone and stirred at 25° C. until full dissolution. 3.22 ml of 5M Sodium hydroxide solution in water was cooled in ice-water bath. To this NaOH water solution, 0.73 ml of 3-mercaptopropanoic acid was added dropwise during 10 minutes. Temperature of the reaction mixture was kept below 10° C. Compound (3) solution in N-methyl-2-pyrrolidone was added and temperature of the reaction mixture was kept below 20° C. The mixture was then heated to 45-50° C. As soon as the temperature of the mixture was reached, 6 ml of water was added and the reaction mixture was stirred for 3 hours at 45-50° C. To the mixture, 4 ml of isopropanol were added. The mixture was cooled to 0-5° C., stirred for 30 min. and filtered. The filtration cake was washed with cold acetone and the product was dried at room temperature to provide Sugammadex in almost 100% yield.

Example 8: Preparation of Sugammadex 1 g of compound of formula (3) prepared according to example 1 was suspended in 8 ml of zdimethylacetamide and stirred at 25° C. until full dissolution. 3.22 ml of 5M Sodium hydroxide solution in water was cooled in ice-water bath. To this NaOH water solution, 0.73 ml of 3-mercaptopropanoic acid was added dropwise during 10 minutes. Temperature of the reaction mixture was kept below 10° C. Compound (3) solution in dimethylacetamide was added and temperature of the reaction mixture was kept below 20° C. The mixture was then heated to 45-50° C. As soon as the temperature of the mixture was reached, 6 ml of water was added and the reaction mixture was stirred for 3 hours at 45-50° C. To the mixture, 4 ml of isopropanol were added. The mixture was cooled to 0-5° C., stirred for 30 min. and filtered. The filtration cake was washed with cold acetone and the product was dried at room temperature to provide Sugammadex in almost 100% yield.

Example 9: Preparation of Sugammadex 1 g of compound of formula (3) prepared according to example 1 was suspended in 8 ml of dimethylformamide and stirred at 25° C. until full dissolution. 3.22 ml of 5M Sodium hydroxide solution in water was cooled in ice-water bath. To this NaOH water solution, 0.73 ml of 3-mercaptopropanoic acid was added dropwise during 10 minutes. Temperature of the reaction mixture was kept below 10° C. Compound (3) solution in dimethylformamide was added and temperature of the reaction mixture was kept below 20° C. The mixture was then heated to 45-50° C. As soon as the temperature of the mixture was reached, 6 ml of water was added and the reaction mixture was stirred for 3 hours at 45-50° C. To the mixture, 4 ml of isopropanol were added. The mixture was cooled to 0-5° C., stirred for 30 min. and filtered. The filtration cake was washed with cold acetone and the product was dried at room temperature to provide Sugammadex in almost 100% yield.

The invention claimed is:
1. A process for preparation of Sugammadex comprising:
a) mixing of γ-cyclodextrin with $CX_4$, in the presence of triphenylphosphine and N-methyl-2-pyrrolidone;
b) treating the reaction product with a base to provide corresponding 6-per-deoxy-6-per-halo-γ-cyclodextrin compound of formula (3),

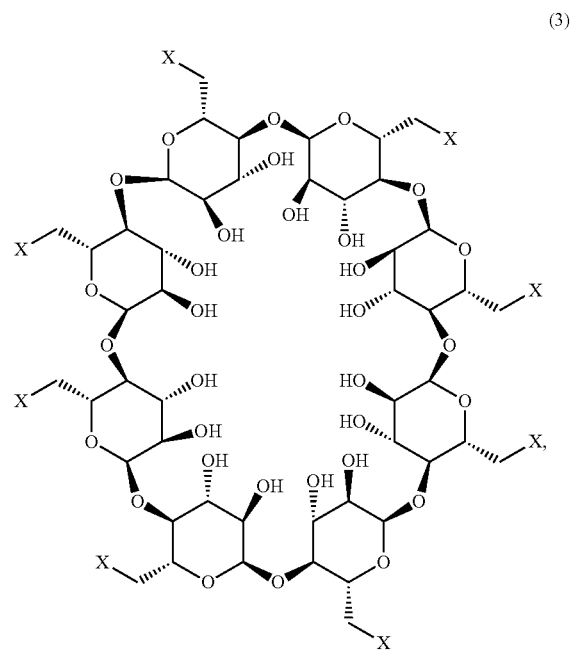

(3)

wherein X is Cl or Br or I; and
c) reacting compound of formula (3) with 3-mercaptopropionic acid in the presence of a sodium base to provide Sugammadex of formula (1),

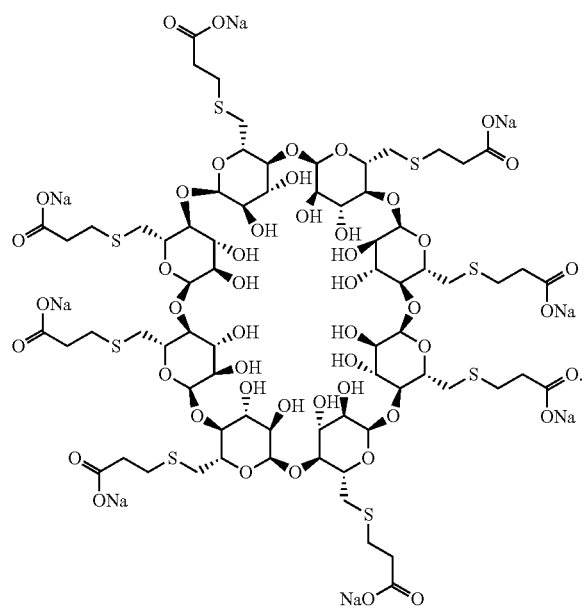

(1)

2. The process according to claim 1 wherein the molar ratio of γ-cyclodextrin to triphenylphosphine ranges from 1:10 to 1:20.

3. The process according to claim 2 wherein the molar ratio of γ-cyclodextrin to triphenylphosphine is 1:15.

4. The process according to claim 1 wherein the concentration of γ-cyclodextrin in N-methyl-2-pyrrolidone ranges from 0.1 to 1 g/ml.

5. The process according to claim 4 wherein the concentration of γ-cyclodextrin in N-methyl-2-pyrrolidone is 0.4 g/ml.

6. The process according to claim 1 wherein mixing of γ-cyclodextrin with $CX_4$ in step a) is done at a temperature lower than 30° C.

7. The process according to claim 1 wherein reaction step a) is done in an organic solvent selected from dichloromethane or methyl-tert-butyl ether or toluene or acetonitrile or THF.

8. The process according claim 1 in which the reaction step c) is done in an organic solvent selected from N-methyl-2-pyrrolidone or dimethylacetamide or dimethylformamide or dimethylsulfoxide.

9. The process according to claim 8 wherein the organic solvent is used together with water.

10. The process according to claim 1 wherein the base in step b) is ammonium hydroxide.

11. The process according to claim 1 wherein X means Br.

12. A process according to claim 1 further comprising the purification of compound of formula (3) wherein the purification comprises:
 suspending the compound of formula (3) in an alcohol, wherein the alcohol is selected from methanol or ethanol or propanol or isopropanol and wherein the alcohol comprises between 3 and 30% (vol/vol) of water;
 b) heating the mixture; and
 c) isolating of compound of formula (3).

13. The process according to claim 12 wherein the alcohol is methanol or ethanol.

14. The process according to claim 12 wherein the alcohol comprises 5% (vol/vol) of water.

15. The process according to claim 12
 wherein the mixture is heated at a temperature between 45° C. and the reflux temperature of the solvent.

* * * * *